United States Patent
Chazot et al.

(10) Patent No.: US 10,537,677 B2
(45) Date of Patent: Jan. 21, 2020

(54) SYSTEM FOR CONTROLLING INJECTORS OF ANAESTHETICS OR SEDATIVES WITH A VIEW TO INDUCING ANAESTHESIA OR SEDATION

(75) Inventors: Thierry Chazot, Groslay (FR); Ngai Liu, Paris (FR); Bernard Trillat, Paris (FR)

(73) Assignee: MEDSTEER, Groslay (FR)

( * ) Notice: Subject to any disclaimer, the term of this patent is extended or adjusted under 35 U.S.C. 154(b) by 370 days.

(21) Appl. No.: 13/144,917

(22) PCT Filed: Dec. 4, 2009

(86) PCT No.: PCT/FR2009/052412
§ 371 (c)(1),
(2), (4) Date: Sep. 27, 2011

(87) PCT Pub. No.: WO2010/081947
PCT Pub. Date: Jul. 22, 2010

(65) Prior Publication Data
US 2012/0010591 A1 Jan. 12, 2012

(30) Foreign Application Priority Data
Jan. 15, 2009 (FR) ...................................... 09 50213

(51) Int. Cl.
*A61M 5/172* (2006.01)
(52) U.S. Cl.
CPC ................. *A61M 5/1723* (2013.01)
(58) Field of Classification Search
CPC .... A61M 5/172; A61M 5/1723; A61M 21/00; A61M 2021/0005; A61M 21/02;
(Continued)

(56) References Cited

U.S. PATENT DOCUMENTS 6,631,291 B2   10/2003   Viertio-Oja et al.
6,801,803 B2   10/2004   Viertio-Oja
(Continued)

FOREIGN PATENT DOCUMENTS

EP   1547631   * 12/2003   ............ A61M 5/172
EP   1547631   *  6/2005
(Continued)

OTHER PUBLICATIONS

Liu et al., Titration of propofol for anesthetic induction and maintenance guided by the bispectral index: closed-loop versus manual control, Anesthesiology, 2006, 104:686-695.*

*Primary Examiner* — Bhisma Mehta
*Assistant Examiner* — Laura C Schell
(74) *Attorney, Agent, or Firm* — Knobbe, Martens, Olson & Bear LLP (57) ABSTRACT

This disclosure relates to a system that comprises means for obtaining a signal representative of the electrocortical activity of the patient, means for analyzing this signal in order to derive from it a signal of depth of anaesthesia, means for monitoring the value and development over time of this signal of depth of anaesthesia, these means being associated with means for calculation of control commands of the injection means, in order to automatically bring the signal of depth of anaesthesia to below a predetermined value during at least one predetermined period of time, in that the means for injection of anaesthetics comprise first means for injection of a hypnotic and second means for injection of a morphinomimetic, in that the means for calculation of the control commands of the injection means comprise means allowing an operator to input a type of induction of anaesthesia chosen from a group of types of induction that differ in terms of the initial concentration of hypnotic, and in that the means for inputting the type of induction comprise means for establishing the initial concentration of hypnotic, (Continued)

which is associated with an initial concentration of morphinomimetic predetermined according to the chosen type of induction.

17 Claims, 2 Drawing Sheets

(58) Field of Classification Search
CPC ........ A61M 2202/048; A61M 2205/33; A61M 2205/333; A61M 2230/10; A61M 2021/0055; A61M 2202/0241; A61M 2205/3303; A61M 2205/3317; A61M 2205/3334
USPC .............................................. 604/65, 66, 67
See application file for complete search history.

(56) References Cited

U.S. PATENT DOCUMENTS

| | | |
|---|---|---|
| 7,089,927 B2 | 8/2006 | John et al. |
| 7,220,240 B2 | 5/2007 | Struys et al. |
| 7,447,541 B2 | 11/2008 | Huiku et al. |
| RE41,291 E | 4/2010 | Viertio-Oja et al. |
| 7,783,343 B2 | 8/2010 | Sarkela et al. |
| 8,512,273 B2 | 8/2013 | Rantala et al. |
| 2002/0082513 A1 | 6/2002 | Ennen et al. |
| 2003/0051737 A1 | 3/2003 | Hickle et al. |
| 2004/0079372 A1 | 4/2004 | John et al. |
| 2006/0009733 A1 | 1/2006 | Martin |
| 2006/0058700 A1 | 3/2006 | Marro et al. |
| 2006/0217628 A1 | 9/2006 | Huiku |
| 2007/0010756 A1 | 1/2007 | Viertio-Oja et al. |
| 2007/0015972 A1* | 1/2007 | Wang .................. A61B 5/0484 600/300 |
| 2007/0276609 A1 | 11/2007 | Greenwald |
| 2007/0282251 A1 | 12/2007 | Barvais et al. |
| 2009/0076339 A1 | 3/2009 | Quintin et al. |
| 2009/0118697 A1 | 5/2009 | Martin |
| 2009/0124867 A1 | 5/2009 | Hirsh et al. |
| 2009/0275853 A1 | 11/2009 | Sarkela |

FOREIGN PATENT DOCUMENTS

| | | |
|---|---|---|
| EP | 1547631 A | 6/2005 |
| JP | 2005 524464 A | 8/2005 |
| WO | WO 03/094726 A1 | 11/2003 |
| WO | WO 2008/059289 A2 | 5/2008 |
| WO | WO 2008/086624 A1 | 7/2008 |

* cited by examiner

Fig. 1

| Type of induction | Type A | | | | Type B | | | | Type C | | | | Type D | | | |
|---|---|---|---|---|---|---|---|---|---|---|---|---|---|---|---|---|
| Plateaus | P1 | P2 | P3 | P4 | P1 | P2 | P3 | P4 | P1 | P2 | P3 | P4 | P1 | P2 | P3 | P4 |
| Index target value | 65 | 56 | 54 | 52 | 65 | 60 | 55 | 52 | 70 | 63 | 58 | 52 | 68 | 64 | 58 | 55 |
| AFB for the hypnotic agent | 50 | 90 | 100 | 100 | 55 | 90 | 100 | 100 | 70 | 100 | 100 | 100 | 70 | 100 | 100 | 100 |
| AFB for the morphinomimetic agent | 35 | 45 | 65 | 100 | 50 | 70 | 100 | 100 | 50 | 70 | 75 | 100 | 50 | 70 | 75 | 100 |
| Low target for the hypnotic agent (μg/mL) | 1,3 | 1 | 1,3 | 1,3 | 1,1 | 1 | 1,2 | 1,1 | 0.7 | 1 | 0.7 | 0.7 | 0.7 | 1 | 1 | 0.7 |
| Low target for the analgesic agent (ng/mL) | 5 | 2 | 2 | 2 | 4.5 | 2 | 2 | 2 | 4 | 1 | 1 | 2 | 3 | 1 | 1 | 2 |
| High target for the analgesic agent (ng/mL) | 12 | 12 | 12 | 12 | 12 | 12 | 12 | 12 | 10 | 10 | 10 | 10 | 10 | 10 | 10 | 10 |
| AFB coefficient of the hypnotic agent | 90 | 65 | 60 | 50 | 90 | 65 | 60 | 50 | 90 | 65 | 60 | 50 | 90 | 65 | 60 | 50 |
| AFB coefficient of the analgesic agent | 92 | 85 | 75 | 70 | 93 | 86 | 76 | 72 | 94 | 87 | 77 | 74 | 95 | 88 | 78 | 75 |
| Additional delay for the hypnotic agent (s) | 120 | 100 | 50 | 30 | 120 | 100 | 50 | 30 | 90 | 120 | 50 | 60 | 90 | 120 | 50 | 60 |
| Additional delay for the analgesic agent (s) | 30 | 35 | 45 | 60 | 30 | 35 | 45 | 60 | 30 | 35 | 45 | 60 | 30 | 35 | 45 | 60 |

FIG.2

SYSTEM FOR CONTROLLING INJECTORS OF ANAESTHETICS OR SEDATIVES WITH A VIEW TO INDUCING ANAESTHESIA OR SEDATION

FIELD OF THE INVENTION

The present invention relates to a system for controlling injectors configured to inject anesthesia or sedation agents in an intravenous anesthesia or sedation mode with a concentration or mass flow rate target, into a patient, with view to inducing this anesthesia or this sedation.

BACKGROUND OF THE INVENTION

General anesthesia for a surgical operation may be defined as a reversible condition, in which the patient should be unconscious by the use of a hypnotic agent, and analgesized by the use of a morphinomimetic agent and whose muscles have to be relaxed by using curares which facilitate the surgical operation.

This general anesthesia is then obtained by gas inhalation or by intravenous injection of anesthesia agents or by association thereof.

The exclusive use of intravenous anesthesia agents is a customary practice. Evaluation of the depth of the anesthesia or the titration of anesthesia agents is accomplished by clinical or paraclinical criteria.

Presently, dosage adaptation of anesthesia agents is achieved with respect to somatic modifications (movements) or those of the autonomous nervous system (tachycardia, hypertension, sweating, pupillary modifications) which are caused by surgery or which show underdosage of a drug.

However, the clinical signs are not always specific or may be absent. The movements are no longer a reliable criterion when curares are used.

Cardiovascular modifications are not specific of anesthesia agents used and may be related to surgery (bleeding, vascular clamping . . . ) or to the patient (arterial hypertension, cardiovascular treatments . . . ).

Intravenous anesthesia with a concentration target also called TCI (Target Controlled Infusion) is a method practiced for titrating the injection of a hypnotic agent or morphinomimetic agent.

This method consists of using a pharmacokinetic model of the agent which calculates a plasma concentration and/or a «effect site» concentration, i.e. at the brain, by assuming that there exists a relationship between the calculated concentration and the effect of the drug.

But, the concentrations calculated with the models have very poor correlation with the clinical condition of the patient and their use has not shown any improvement in the management of post-operative patients as compared with a standard use (i.e. in a mass perfusion) of the same anesthetic agents.

The advantage of TCI tools is to provide the physicians with the possibility of faster dosage adaptations than evolutions expressed in mass concentrations.

The presence of an anesthesiologist therefore remains indispensable during anesthesia.

However, an anesthesiologist is not always available in emergency situations, in military conflicts or when the patient cannot be moved.

A method of measuring the depth of the anesthesia or the effect of the anesthesia agents is to measure the electrocortical activity or the electroencephalogram (EEG) of the patient.

The anesthesia agents modify the morphology of the EEG signal in a way specific to each agent. However, only experienced electroencephalographists may detect these modifications. Measurement of the EEG was especially used in anesthesia during research procedures for quantifying the effect of anesthesia agents.

The real-time interpretation of changes in the EEG in the operating theatre was facilitated by the arrival of monitors which allow real-time analysis of this EEG signal. These monitors calculate different parameters from the spectral analysis of the EEG and combine them in order to provide a signal or index of anesthetic depth.

The BIS monitor of Aspect Medical System Inc. is used for measuring the anesthetic depth by calculating an index from a bi-spectral analysis of the EEG. This index varies from 0 to 100, 0 representing an isoelectric or flat line and 100 representing a line for a patient wide awake. During anesthesia, the recommendation is to maintain this index in an interval between 45 and 60 in order to obtain satisfactory conditions for performing a surgical operation. Such a monitor allows measurement of the anesthetic depth and titration of the hypnotic agent.

Indeed, it has already been suggested to use this BIS index for administering an intravenous hypnotic agent in a closed loop while sustaining anesthesia (see, for example, document U.S. Pat. No. 7,220,240), or during induction and sustainment of general anesthesia.

In the state of the art, there exists another monitor such as for example the Entropy monitor of Datex-Ohmeda Inc. This monitor quantifies disorder, i.e. entropy, in the EEG signal, this signal for an anesthetized patient being characterized by extensive, synchronized and ordered waves with little disorder and therefore low entropy.

It is then sufficient to maintain this index in the interval 40 to 60 in order to obtain satisfactory conditions for performing the surgery. This monitor provides two pieces of information, the first being called the "State Entropy (SE)" information which measures the depth of hypnosis and the second one being called the "Response Entropy (RE)" which measures the anti-nociception deficit. This monitor has already been proposed for automated perfusion of a hypnotic agent (see document U.S. Pat. No. 6,631,291, for example).

SUMMARY OF THE INVENTION

The goal of the invention is to optimize the use of these injection systems for injecting anesthetic or sedative agents.

For this purpose, the object of the invention is a system for controlling injectors configured to inject anesthesia or sedation agents in an intravenous anesthesia or sedation mode with a concentration or mass flow rate target, into a patient, with view to inducing this anesthesia or this sedation, including:
  a detector for acquiring a signal representative of the electrocortical activity of the patient,
  an analyzer for analyzing the signal so as to extract therefrom an anesthetic depth signal,
  a tracker for tracking the value and the time-dependent evolution of this anesthetic depth signal, associated with a computer for computing control signals for the injectors, in order to automatically bring the anesthetic depth signal below a predetermined value for at least one predetermined period of time,
wherein:
  a first injector is configured to inject a hypnotic agent, and a second injector is configured to inject a morphinomimetic agent, wherein:
the computer for computing control signals for the injectors comprises a data input device configured to receive input by an operator of a type of anesthesia induction selected from a set of induction types being different by the initial concentration of hypnotic agent, wherein:
the data input device is configured to determine the initial concentration of hypnotic agents, with which is associated a predetermined initial concentration of a morphinomimetic agent depending on the selected induction type.

According to other aspects, the system according to the invention has one or more of the following features:
the computer is configured to determine intermediate target values of an anesthetic depth signal in order to define plateaus during the induction phase;
the computer is adapted so as to establish three intermediate values of anesthesia plateaus;
the first injector is configured to receive control signals at a first frequency and the second injector is configured to receive control signals at a second frequency different from the first frequency;
the second frequency is higher than the first frequency;
it includes a data input device configured to receive input by an operator the target value of the anesthetic depth signal wherein the computer is configured to determine a target value,
the computer is configured to limit and/or inhibit control signals in opposite directions of the first and second injectors,
the computer is adapted so as to increase the concentration of hypnotic agents after a predetermined number of modifications of the morphinomimetic agent concentration in order to bring back the anesthetic depth signal into the predetermined range around the target value,
the predetermined number of modifications is equal to three,
the computer is adapted so as to compute the difference between the current value of the anesthetic depth signal and the target value, and to compare this difference with predetermined threshold values in order to, when the current value of the anesthetic depth signal is above the threshold value:
when the difference is less than a first threshold, act with priority on the concentration of morphinomimetic agent by increasing it,
when the difference is greater than the first threshold and less than a second threshold, increase the morphinomimetic agent concentration and increase that of the hypnotic agent in a small proportion, and
when the difference is greater than the second threshold, increase the morphinomimetic agent concentration and that of the hypnotic agent in a greater proportion,
in order to bring the value of the anesthetic depth signal back into the predetermined range,
the computer is adapted to compute the difference between the current value of the anesthetic depth signal and the target value, and this in order to compare this difference with predetermined threshold values if the signal is less than the target value in order to, when the current value of the anesthetic depth signal is below the target value:
when the difference is less than a third threshold, act with priority on the morphinomimetic agent concentration by reducing it,
when the difference is less than the third threshold and greater than a fifth threshold, reduce the concentration of morphinomimetic agent and reduce that of the hypnotic agent in a small proportion, and
when the difference is less than the fourth threshold, reduce the morphinomimetic agent concentration and that of the hypnotic agent in a greater proportion,
in order to bring the value of the anesthetic depth signal back into the predetermined range,
the computer is configured to determine high and low limiting values of concentrations of hypnotic and morphinomimetic agents,
the computer includes a data input device so that the operator may manually input high and low limiting values of the concentrations of the hypnotic and morphinomimetic agents,
the computer includes a disabler configured to disable the computer in order to allow the operator to manually take over control of the injectors,
the computer is configured to maintain the control signals at their last value before a loss of the electrocortical activity signal,
the computer includes sound and/or visual alerts configured to warn the operator in the case of loss of the electrocortical activity signal, and
the injectors comprise motorized controllers.

BRIEF DESCRIPTION OF THE DRAWINGS

The invention will be better understood with the description which follows only given as an example and made with reference to the appended drawings wherein.

DETAILED DESCRIPTION OF THE PREFERRED EMBODIMENT

Figure 1:
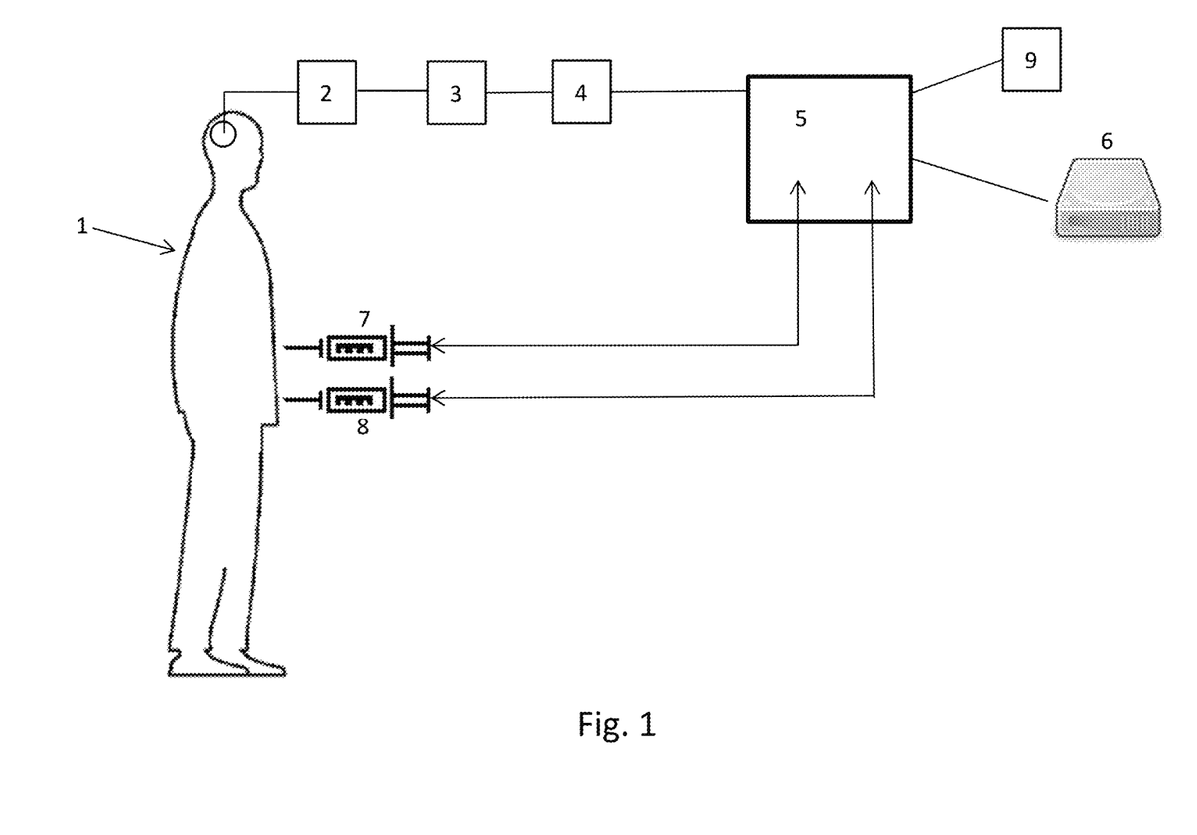
FIG. 1 illustrates a block diagram of the structure and of the operation of a control system according to the invention.

Indeed, a system for controlling injectors configured to inject anesthesia or sedation agents in an intravenous anesthesia or sedation mode with a concentration or mass flow rate target, into a patient, with view to inducing and maintaining this anesthesia or this sedation, is illustrated in this FIG. 1.

In this figure, the patient is designated by the general reference 1 and the system then includes a detector (2) for acquiring a signal representative of the electrocortical activity of the patient.

The output of the electrocortical activity tracker is connected to an analyzer (3) configured to analyze the corresponding signal in order to extract therefrom an anesthetic depth signal.

As an example, the analyzer may for example deliver a signal in the form of a BIS or entropy index, as this was indicated earlier.

The output of the analyzer is connected to a tracker (4) configured to track the value and the time-dependent evolution of this anesthetic depth signal, associated with the computer (5) configured to compute signals for controlling the injectors, allowing automatic closed loop regulation of the anesthetic depth signal in a predetermined range around a target value. A data input device (9) is configured to receive input by an operator.

The tracker is designated by the general reference 4 in this figure and for example comprises any suitable computer 5, associated with stored information, designated by reference 6.

In fact, the injectors comprise a first injector configured to inject a hypnotic agent receiving control signals at a first frequency, designated by the general reference 7 in this figure and injecting second injector configured to inject a morphinomimetic agent receiving control signals at a second frequency, different from the first frequency, being designated by the general reference 8 in this figure. Further, the first injector 7 and the second injector 8 are configured to send back information on the amount of administered agent, respectively of the hypnotic agent and of the morphinomimetic agent, and a controller regularly makes sure that the signals are executed.

It will be noted that the second frequency is higher than the first frequency in the illustrated embodiment.

Thus, the control system according to the invention provides control of the injection of the hypnotic and morphinomimetic agents, from the same BIS or entropy index signal for inducing and maintaining anesthesia or sedation by maintaining a stable anesthetic depth level.

This is also achieved by using a controller of the CLASS (Closed-Loop Anesthesia Safety System) type, which controls the injectors in the TIC mode, by using the information which stems from the tracker after analyzing the EEG activity of the patient.

The information delivered by the tracker comprises:
the quality index of the signal,
the absolute value of the index for example recorded every five seconds,
the value of the EMG (for Electromyogram) or the RE (Response Entropy),
the presence and the quantification of BSR (Burst Suppression Ratio),
slope of the variation of the index.

The computer measures and then computes from this index, by using successive time windows:
the time-dependent evolution of the oscillations in frequency and in amplitude,
the time percentage comprised in the interval 40-60,
the time percentage of values less than 45,
the time percentage of values above 55.

The CLASS controller is of the controller/regulator type, a Proportional Integral Derivative (PID) controller, i.e. a control member with which it is possible to carry out closed-loop regulation of an industrial system. PID regulators are the most used in servo-controlled systems. The PID allows three simultaneous actions on the error between the target (or set value) and the measurement:
a proportional action: the error is multiplied by a gain $K_c$ (gain of the controller),
an integral action: the error is integrated over a time interval $T_i$, called integral time, and
a derived action: the error is derived according to a time $T_d$, called derived time.

If time is a continuous variable, the PID controller is described by the following equation (1):

$$u(t) = K_c e(t) + \frac{K_c}{T_i} e(t) \int_0^t e(t)dt + K_c T_d + K_c T_d \frac{de(t)}{dt} \quad (1)$$

When time becomes a discrete and digitized variable (for example if the concentration is maintained constant between two measurements of the BIS), the PID may be written according to equation (2):

$$u(t) = u(t - T_s) + K_c[e(t) - e(t - T_s)] + \\ \frac{K_c T_s}{T_i} e(t) + \frac{K_c T_d}{T_s}[e(t) - 2e(t - T_s) + e(t - 2T_s)] \quad (2)$$

wherein $T_s$ represents the time interval between the measurements for such a digitized PID controller.

In these two equations (1) and (2), u(t) is the output of the controller and $e(t) = y_{sp} - y(t)$ is the Index Error wherein $y_{sp}$ is the target (or set value, known as «set point»).

The controller modifies the target concentration at the effect site, noted as Ce, of a hypnotic agent such as Propofol or of a morphinomimetic agent such as Remifentanil for maintaining the BIS to a target of 50, for example. The algorithm may be broken down into two terms: a term for amplifying the correction (AFB) and a feedback action term (Feed-forward).

The CLASS controller has a cascade structure which integrates the following elements:
1/ The Index Error
The Index Error is computed every five seconds for example and represents the difference between the measured index and the rated index, i.e. the one which is desired. This rated index may be inputted by an operator, and then represents the target value of the anesthetic depth signal. It may also be established by means for determining a target value by default, for example 50. If the Index Error is different from zero, a modification of the concentration of the agents is made after a predetermined waiting time.
2/ The Delay Between Each Modification
A refractory period or delay between each modification should be observed. This delay is initially computed by the pharmacokinetic model of each anesthesia agent. For example Schnider's model may be selected for the hypnotic agent and Minto's model for the morphinomimetic agent. The delay between each concentration modification then depends on the time required for attaining the concentration at the effect site computed by the model. Between each modification, the controller waits for the time required for reaching the calculated concentration at the effect site. To this theoretical time, is added a variable additional delay which depends on the last concentration modification. When the concentration modifications are small, the equilibrium or stabilization delay at the effect site is longer and an additional delay is added which varies from five seconds to two minutes, for example.

In the case of the morphinomimetic agent, each command for lowering the target value induces an increase in the additional delay and a decrease of the triggering threshold for fresh lowering. The first command for increasing the target value resets the additional delay and the threshold for triggering lowerings of the target value.

On the other hand, if the feedback action («Feed-forward») is enabled, the latter has priority and a concentration modification may be triggered automatically and immediately.
3/ Amplification of the Correction (AFB for "Amplification of the FeedBack")
The amplification of the correction is the gain which allows modification of the concentration. This correction is possible if the quality index of the signal is greater than 50%.

The correction depends on the Index Error, on the EMG activity, on the anesthetic agent and on the feedback. The AFB modifies the concentration according to the following formula:

(new concentration)=(present concentration)×(1+ Index Error/AFB)

The correction may be expressed as:

$$C_e(t) = C_e(t - T_s)\left[1 - \frac{e(t)}{AFB}\right]$$

wherein:
 −e(t) is the Index Error, with e(t)=BIS$_{sp}$−BIS(t), and
 $T_S$ is the minimum time between two concentration modification periods. It is equal at least to the time required for reaching the peak of the effect of the drug. This delay is adjusted from 5 to 120 seconds depending on the last correction. A preceding low amplitude correction increases the delay of the following modification.

If the following replacement is performed in the preceding equation, u(t)=C$_e$(t), y(t)=BIS(t) and y$_{sp}$=BIS$_{sp}$, the correction may be written as:

$$u(t) = u(t - T_s)\left[1 - \frac{e(t)}{AFB}\right] \quad (3)$$

By comparing equations (2) and (3) it is then possible to note that the controller of the correction is an integral function and that the gain is a function of the u(t−T$_S$) type:

$$\frac{K_c T_d}{T_i} = \frac{C_e(t - T_s)}{AFB} \quad (4)$$

The increase in the concentration of the anesthesia agents is all the more significant since the Index Error is significant. However, the variations of concentration are limited during the decreasing phases of the latter in order to avoid refractory periods for example of more than three minutes. The AFB is specific to each agent, to the anesthesia phase (induction or maintenance), to each Index Error and to the current concentrations of the agents. The determination of the AFB depends on the sign and on the significance of the Index Error.

4/ Feedback Action (Feed-Forward)

This function allows amplification of the correction of the concentration. In the hierarchy of the CLASS controller, feed-forward has priority and may occur at any time.

This function is inhibited if the quality index of the signal is less than 50, if the average percentage of the BSRs (according to the acronym «Burst Suppression Ratio») is greater than 5% during the last four minutes, and if the EMG activity is greater than 47 dB, which is then considered as an artifact, a correction amplification is in progress and if it is the phase or inducing anesthesia.

This function is enabled during the phase for maintaining anesthesia, if the measured index is greater than 60 or if the Index Error (−e(t)) is greater than 10, if the slope of the index increases by more than 10 points in less than 15 seconds for example, or if the EMG activity exceeds 41 dB for the hypnotic agent such as Propofol and 37 dB for the morphinomimetic agent such as Remifentanil. Finally, this function may be enabled by oscillations of the index or of the EMG activity.

The condition may then be expressed as e(t)−2e(t−1)+e(t−2)>10 with one measurement every five seconds.

When feed-forward is enabled, a concentration correction is made immediately with an AFB proportional to the Index Error and to the concentration of the current agents: AFB=−e(t)·EMG·u(t−T$_S$) wherein $$u(t) = u(t - T_s)\left[1 - \frac{e(t)}{AFB}\right] = u(t - T_s)\left[1 + \frac{1}{EMG \cdot u(t - T_s)}\right],$$

which gives:

$$u(t) = u(t - T_s) + \frac{1}{EMG}$$

Further, if the current concentration is low, the controller determines a default concentration in order to avoid too small modifications. For example:
 if the concentration of the current hypnotic agent is less than 1.3 µg/ml, the enabling of this function causes a minimum increase in concentration to 1.8 µg/ml of the target value at the effect site, and
 if the current morphinomimetic agent concentration is less than 4 µg/ml, enabling of the function causes at least an increase to 4 µg/ml of the target value at the effect site.

5/ Interaction Rules Between the Hypnotic and Morphinomimetic Agents

In the system according to invention, there are therefore two controllers, one for the hypnotic agent and the other one for the morphinomimetic agent. Both of these controllers are enabled at the same time during induction of anesthesia, and they then operate independently.

As the pharmacokinetic properties of a morphinomimetic agent, of the Remifentanil type for example, are different from those of a hypnotic agent of the Propofol type for example, the delay between each modification is shorter, the added waiting times are shorter and the triggering conditions are closer around the target index value for the morphinomimetic agent as compared with those for the hypnotic agent. The result is that modifications for the morphinomimetic agent are generally more frequent than for the hypnotic agent in the absence of enabling of the feedback function.

Moreover, interaction rules are enabled in order to limit or even avoid decisions and control signals in opposite directions of the first and second injectors. Thus, when the concentration of morphinomimetic agent increases, the controller limits the possibility of a decrease in the hypnotic agent concentration. Also, when the morphinomimetic agent concentration decreases, the controller limits the possibility of an increase in the hypnotic agent concentration. When it is the hypnotic agent concentration which increases, the controller limits the possibility of a decrease in the concentration of the morphinomimetic agent. Also, if the hypnotic agent concentration decreases, the controller limits the possibility of an increase in the morphinomimetic agent concentration.

Large amplitude or repeated variations of a concentration of one of the agents lead to preventing inverse concentration variations of the other agent by temporarily setting the lower limit of the concentration of this agents to the current value.

Moreover, if there are more than three successive positive modifications (increases) for example of the morphinomimetic agent concentration, a positive correction of the hypnotic agent concentration is carried out. Of course, a different number of successive modifications may be contemplated.

6/ Administration of the Agents in the TIC Mode

The administration of anesthesia agents in the targeted concentration intravenous anesthesia mode (TIC) is a method which has been used in clinical practice for years and which applies a perfusion pump associated with a microprocessor. The program of the microprocessor then contains the pharmacokinetic model which models the removal and the metabolism of the drug.

By giving the age, sex, weight, size of the patient and the desired plasma concentration, the integrated program computes and administers a drug bolus required for obtaining the desired concentration.

With it, it is also possible to retain a stable computed theoretical concentration.

The program also allows computation of the theoretical time required for obtaining a new plasma concentration at the effect site.

If the quality index of the signal is less than 50%, the tool maintains the last selected concentration. The system then allows real-time display of the computation of the theoretical plasma concentrations and at the effect site, the concentration selected by the tool, the concentration curves, the delay of the next modification if necessary and the mass flow rate. This then gives the possibility of computing the time required for reaching equilibrium of the selected target concentration, evaluated by the pharmacokinetic model used.

In the system according to the invention, there are in fact two PID type controllers which have the same structure and one of which controls the concentration of hypnotic agent and the other one that of morphinomimetic agent, simultaneously from information which stems from the same index signal. In the absence of enabling of feed-forward or of the interaction rules and if a waiting time is observed between two modifications, the controller may decide to modify a concentration.

As the action delay given by the pharmacokinetic model is faster for morphinomimetic agents such as Remifentanil, the concentrations of this agent are more frequently modified than those of the hypnotic agent such as Propofol. This modification depends on the sign of the Index Error. A positive Index Error causes an increase in concentration and a negative Index Error causes a decrease in concentration.

If the Index Error is less than ±2 for the morphinomimetic agent and then ±3 for the hypnotic agent, there is no modification. Beyond indicated values of Index Error, the controller makes a modification. An AFB and a specific delay for both agents are assigned to each Index Error value.

The concept of automatic handling of the morphinomimetic agent is based on the fact that low index variations prefigure larger variations and are ascribable to a particular analgesia defect rather than to a hypnotic agent deficit. The adjustment parameters have therefore been established so that the reactivity of the morphinomimetic system is greater than that of the hypnotic system. The number of concentration changes in the morphinomimetic agent is therefore larger than that in the hypnotic agent because of a shorter refractory period between each modification and a lower triggering threshold. The closed loop behavior of the hypnotic agent is then to avoid having an index below 40 or above 60.

The CLASS controller then records information from the tracker and the injectors, which may for example appear as motorized injectors, such as electric syringes.

As this was indicated earlier, the pieces of information to be provided during the starting up of the system are the age, size, weight, sex of the patient and the anesthesiologist determines the first concentration of hypnotic agent. The system then computes the first concentration of the morphinomimetic agent. Thus, this system allows the index to be maintained for example in an interval from 40 to 60.

The algorithm integrated in the CLASS controllers include two specific portions, one for the phase inducing anesthesia and the other one for the phase maintaining the latter. The switching between both phases is accomplished automatically.

The system according to the invention allows the induction phase to be carried out automatically, which is defined as the time period between the beginning of the administration of the agents and the holding of the EEG signal for at least 30 seconds below the value 60, for example.

The only decision made by the user is then to select the first concentration of hypnotic agent such as Propofol between 1 and 5 µg/ml. In fact, the user thus selects an anesthesia induction type from a set of induction types which differ by the initial concentration of hypnotic agent. The controller then automatically determines the first concentration of morphinomimetic agent such as Remifentanil in connection with the concentration of hypnotic agent requested by the user, and predetermined according to the selected induction type.

For example, four different types of induction may be contemplated: inductions of type A, of type B, of type C, and of type D. The different types of induction are distinguished by:

the value of the first target concentration of morphinomimetic agent such as Remifentanil, the values of the waiting delay times after reaching the target concentration equilibrium of each agent, and the thresholds of index values which determine the change of plateau.

The principle of the thereby designed induction is based on the idea that the physician in charge of the patient is able to evaluate the risk related to overdosage of anesthetic agents during the induction. It is common sense that the higher the risk, the lower should be the value of the initial target concentration. Accordingly, the first value of a target concentration of morphinomimetic agent such as Remifentanil is indexed to the first value of the target concentration of hypnotic agent such as Propofol.

The induction of type A may be used for patients who do not have major problems and for whom a moderate overdosage of hypnotic does not pose any problems. What is requested is a fast induction sequence. The concentration of hypnotic agent such as Propofol is greater than 2.8 µg/ml, the first concentration of morphinomimetic agent such as Remifentanil is then of the order of 5 ng/ml.

The induction of type B may be used for patients having minor problems for whom it is desired to avoid overdosage which may cause arterial hypotension. In this case, the requested concentration of hypnotic agent such as Propofol, may be comprised between 2.4 and 2.8 µg/ml, the first concentration of a morphinomimetic agent such as Remifentanil being of the order of 5 ng/ml.

The induction of type C may be used for fragile patients for whom it is attempted to obtain induction with little hemodynamic change. This is a slow induction sequence. In this case, the requested concentration of hypnotic agent such as Propofol is comprised between 2.1 and 2.4 µg/ml, the first concentration of morphinomimetic agent such as Remifentanil then being of the order of 4 ng/ml.

The induction of type D may be used for particularly fragile patients or during management of already sedated intensive-care patients. This type of induction is selected by a first target concentration of hypnotic agent such as Propofol of less than or equal to 2.1 µg/ml.

Moreover, the system also includes a computer configured to determine intermediate values of anesthetic depth signal in order to define plateaus during the induction phase, for example for the four types of induction.

The system then uses as an input signal the quality index of the signal, the absolute value of the index for example recorded every five seconds, the EMG value and the Index Error.

According to the type of induction and the plateau, the AFB values, the delay and rated index values are specific.

For example, three intermediate values of anesthesia plateaus may be contemplated.

The goal of the system is then to establish a first plateau with a rated index equal to 80 for example. The measured index is then weighted depending on the EMG activity and the value of the index is reduced if this EMG activity is high and depending on the measured value of the index. The waiting times before a fresh modification are then set. These times vary from 15 to 120 seconds but a maximum delay between two target concentration variations or per induction plateau is set.

Figure 2:
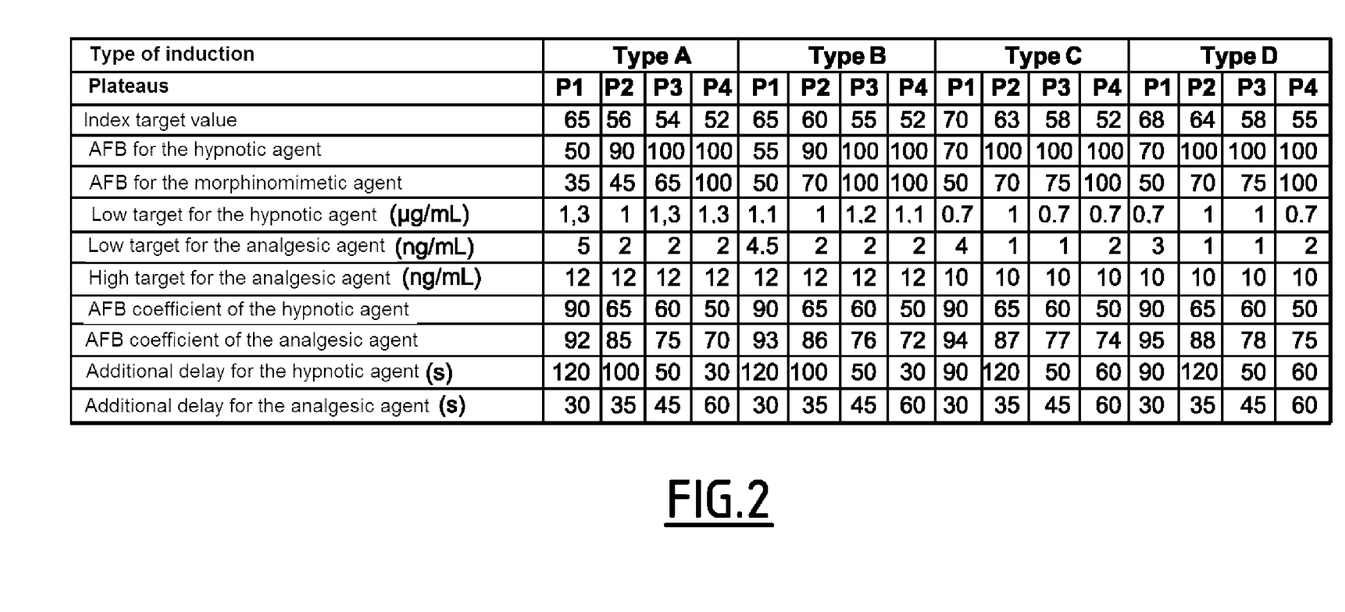
FIG. 2 illustrates a table of steps for inducing anesthesia.

The steps of the induction for a hypnotic agent such as Propofol and a morphinomimetic agent such as Remifentanil may be summarized in the table of FIG. 2.

Generally:
  if the Index Error is negative then the concentration is reduced proportionally by AFB,
  if the Index Error is comprised between 0 and 10 with a rated index of 80, the concentration is then not modified and delays as earlier are expected, and
  if the Index Error is greater than 10, the concentration of both agents is then increased.

The second plateau is as for it guided with a rated index of 70.

The third plateau may be established with a rated index of 60 and rules identical with those of the other plateaus in order to wait for expiry of the predetermined delays.

In fact, an additional delay may be added to the time computed by the model. This additional delay depends on the type of induction.

At the end of the induction phase which is defined as being the period between the beginning of the administration of the anesthetic agents and the maintaining of the anesthetic depth signal, at least 30 seconds below a value for example equal to 60, the CLASS controller switches to the maintenance phase. The maintenance phase may be described according to the observation of the incoming signal which comprises:
  the quality index of the signal,
  the absolute value of the index for example recorded every 5 seconds,
  the value of EMG or RE,
  the presence and the quantification of BSRs,
  the slope of the variation of the index, and
  the measurement and computation from the index, by using successive time windows, of:
    the time-dependent evolution of the oscillations in frequency and in amplitude (as described earlier),
    the time percentage comprised in the interval 40-60,
    the time percentage of the values below 45, and
    the time percentage of the values above 55.
  Further, are also taken into account:
    the time-dependent evolution in the targets of the two anesthetic agents through successive time windows, and
    the ratio between the current target value of each agent and the maximum authorized value.

Also, the time required for reaching the equilibrium of the selected target concentration and the continuous time spent at the lower limit of either one of the agents may also be recorded.

Indeed, the data input device is configured to input the high and low limiting concentration values of the agents may be defined, e.g. the data input device being configured so that the operator can manually input high and low limiting values.

Thus for example, during the closed loop use, these minimum and maximum values are for example 1.3 and 5 µg/ml for the hypnotic agent such as Propofol and 3 and 15 ng/ml for the morphinomimetic agent such as Remifentanil. These values themselves also depend on the type of induction. They are smaller when passing from type A to type D:
  from 1.3 to 0.7 µg/ml for the lower limit of the hypnotic agent such as Propofol, and from 3 to 2 ng/ml for the lower limit of the morphinomimetic agent such as Remifentanil, and
  from 8 to 12 ng/ml for the upper limit of the morphinomimetic agent such as Remifentanil, the upper limit for the hypnotic agent such as Propofol being always 5 µg/ml.

At any moment, the user may decide to modify these limiting values, and at any moment during the use of the CLASS controller, the time spent at the lower limit of either one of these agents, the time-dependent evolution of the concentrations of both agents through successive time windows and the ratio between the current target value of each agent and the maximum authorized value are recorded.

The processing of the oscillations is accomplished over a period of four minutes by measuring the frequency and the amplitude of the oscillations of the BIS, an oscillation being a sequence of two variations of the BIS in opposite directions over a period of five seconds (increase followed by decrease or vice versa).

In the case of large amplitude oscillations, i.e. when the oscillation amplitude is greater than a first threshold, a set increase in the concentration of hypnotic agent is triggered at the third oscillation. The size of this increase is indexed to the current target of the agent. This increase is all the smaller since the hypnotic agent target value is high. This variation in the hypnotic agent concentration is conditioned to the absence of BSRs and to a low number of index values below the tolerance interval. This triggering blocks that of the feedback actions.

When the oscillations are of low amplitude, three thresholds are defined which trigger different actions if they are reached in the four-minute time window. The processing of the oscillations then consists of determining the agent on which the system acts by making a comparison between the current target value and the maximum authorized target value at the moment of the determination for each agent. This standpoint aims at avoiding a disequilibrium between both main anesthesia agents, the action of which is known to be synergistic. In this case, one will then preferentially act on the agent for which the current target value/maximum target value ratio is the smallest:
  if this is the morphinomimetic agent:

at the first threshold reached by the amplitude of the oscillation, the concentration of morphinomimetic agent can no longer decrease, at the second threshold reached, the AFB of the morphinomimetic agent is reduced so as to enhance the next reaction, and at the third threshold, a set increase is immediately determined.

if this is the hypnotic agent:

at the first threshold reached, the hypnotic agent concentration can no longer decrease, at the second threshold reached, the AFB of the hypnotic agent is decreased in order to enhance the next reaction, and at the third threshold, a set increase is determined immediately. Within a window of four minutes, there may be more than three triggerings of this function.

The amplitude of the correction decreases from the first to the third triggering threshold. This function is only triggered if the BSRs are not too high.

The controller then includes a suitable computer configured to compute the difference between the current value of the anesthetic depth signal and the target value, and for comparing this difference to predetermined threshold values in order to, when the current value of the anesthetic depth signal is above the target value:

when the difference is less than a first threshold, act with priority on the concentration of the morphinomimetic agent by increasing it, when the difference is greater than the first threshold and less than a second threshold, increase the concentration of morphinomimetic agent and increase that of the hypnotic agent in a small proportion, and when the difference is greater than the second threshold, increase the concentration of morphinomimetic agent and that of the hypnotic agent in a larger proportion, and this in order to bring the value of the anesthetic depth signal back into the predetermined range.

Also, when the current value of the anesthetic depth signal is below the target value:

when the difference is less than a fourth threshold, the controller acts with priority on the concentration of morphinomimetic agent by reducing it, when the difference is less than the fourth threshold and greater than a fifth threshold, it acts by reducing the concentration of morphinomimetic agent and by reducing that of the hypnotic agent in a small proportion, and when the difference is less than the fifth threshold, it acts by reducing the concentration of morphinomimetic agent and that of the hypnotic agent in a larger proportion, and this for bringing the value of the anesthetic depth signal into the predetermined range.

It is then conceivable that different actions may be generated by the CLASS controller, i.e.:

proportionally increase the target value of either one of the agents, proportionally decrease the target value of either one of the agents, increase the waiting time after modification of the target value, reduce the waiting time after modification of the target value, modify the hierarchy of the current actions, increase the value of the rated index, decrease the value of the rated index, block the decrease of the concentration of hypnotic agent such as Propofol, block the decrease of the concentration of morphinomimetic agent such as Remifentanil, increase in fixed amounts the concentration of hypnotic agent such as Propofol, increase in fixed amounts the concentration of morphinomimetic agent such as Remifentanil, displace the limits of the tolerance interval of the values of the index, amplify the correction relatively to the basic computations, and temporarily modify the lower limit for example of the morphinomimetic or hypnotic agent.

Moreover, safeties are also set up. For example a disabler configured to disable control of the injectors by the computer may be contemplated, in order to allow the operator to manually take over control of the injectors.

Also, wherein the computer configured to control the injectors is configured to maintain the control signals at their last value before loss of the electrocortical activity signal, may be contemplated, the controller, for example being configured to alert the operator (e.g., by sound or visual means) in case of a loss of the signal.

At any moment, the user may administer anesthesia agents in a manual mode.

These different features may be applied by software programs integrated into the computer 5.

It is then conceivable that such a system gives the possibility of simultaneously administering a hypnotic agent such as Propofol and a morphinomimetic agent such as Remifentanil in a closed loop, and this is servo-controlled from a single electrocortical activity signal of the patient.

A CLASS controller allows induction and maintenance of the general anesthesia, sedation of the postoperative period and sedation for intensive-care patients.

It uses as an incoming signal, the electrocortical activity provided by a tracker for example of bi-spectral index or entropy, which allows measurement of the depth of the anesthesia.

The invention claimed is:

1. A system for inducing and maintaining anesthesia or sedation in a patient comprising injectors, wherein the system controls injection by the injectors of anesthesia or sedation agents in an intravenous anesthesia or sedation mode with a concentration or mass flow rate target, the injectors comprising:

a first injector configured to inject a hypnotic agent, and a second injector configured to inject a morphinomimetic agent, the system comprising:

a detector configured to acquire a signal representative of electrocortical activity of the patient, an analyzer configured to analyze the signal representative of electrocortical activity in order to extract therefrom an anesthetic depth signal, a tracker configured to track a value and time-dependent evolution of the anesthetic depth signal, wherein the tracker is associated with a computer adapted to compute control signals for two specific phases of inducing and maintaining anesthesia: a first phase for induction of anesthesia and a second phase for maintenance of anesthesia, the control signals being computed only based on the anesthetic depth signal obtained from the signal representative of electrocortical activity and a first concentration of the hypnotic agent, the control signals being for:

during the induction phase of anesthesia, triggering injection of the hypnotic agent and the morphinomimetic agent by the first and second injectors, respectively, based on the tracked anesthetic depth signal, in order to automatically bring the anesthetic depth signal below a predetermined value for at least 30 seconds, wherein the induction phase of anesthesia is defined as a period between a beginning of administration of the hypnotic agent and the morphinomimetic agent, and maintaining of the anesthetic depth signal at least 30 seconds below the predetermined value, the predetermined value being equal to 60, and during the maintenance phase of anesthesia, automatically closed loop regulating the anesthetic depth signal within a predetermined range around a target value, and wherein the computer comprises a data input device configured to receive input from an operator regarding a type of anesthesia induction selected from a plurality of discrete induction types that correspond to a health state of the patient, wherein the plurality of discrete induction types are distinguished by waiting delay times after reaching a target concentration equilibrium of each agent and by thresholds of index values that determine a change of plateau, said plurality of discrete induction types also differing from each other by an initial concentration of the hypnotic agent, and wherein the computer is configured to determine both (i) an initial concentration of the morphinomimetic agent and (ii) intermediate concentrations of the morphinomimetic agent and the hypnotic agent in order to determine intermediate target values for the anesthetic depth signal in order to define induction plateaus of anesthesia during the induction phase based on the type of anesthesia induction input into the data input device, a time between each induction plateau being between 15 to 120 seconds.

2. The system according to claim 1, wherein the computer configured to determine the intermediate target values for the anesthetic depth signal is configured to establish three intermediate values of anesthesia plateaus.

3. The system according to claim 1, wherein the first injector for injecting the hypnotic agent is configured to receive the control signals at a first frequency and wherein the second injector for injecting the morphinomimetic agent is configured to receive the control signals at a second frequency different from the first frequency.

4. The system according to claim 3, wherein the second frequency is higher than the first frequency.

5. The system according to claim 1, wherein the data input device is configured to receive input from the operator of the target value of the anesthetic depth signal.

6. The system according to claim 1, wherein the computer is configured to limit and/or inhibit the control signals in opposite directions of the first and second injectors.

7. The system according to claim 1, wherein the computer is adapted for increasing a concentration of the hypnotic agent after a predetermined number of modifications of a morphinomimetic agent concentration for bringing back the anesthetic depth signal into the predetermined range around the target value.

8. The system according to claim 7, wherein the predetermined number of modifications is equal to three.

9. A method of bringing a value of an anesthetic depth signal back into a predetermined range comprising:

providing the system according to claim 1, wherein the computer is adapted for computing a difference between a current value of the anesthetic depth signal and the target value, and for comparing this difference with predetermined difference threshold values, and optionally when the current value of the anesthetic depth signal is above the target value, increasing with priority the intermediate concentration of the morphinomimetic agent when the difference is less than a first predetermined difference threshold, increasing the intermediate concentration of the morphinomimetic agent and increasing the intermediate concentration of the hypnotic agent in a small proportion when the difference is greater than the first predetermined difference threshold and less than a second predetermined difference threshold, or increasing the intermediate concentration of the morphinomimetic agent and increasing the intermediate concentration of the hypnotic agent in a larger proportion when the difference is greater than the second predetermined difference threshold, wherein the value of the anesthetic depth signal is brought back into the predetermined range.

10. A method of bringing a value of an anesthetic depth signal back into a predetermined range comprising:

providing the system according to claim 1, wherein the computer is adapted for computing a difference between a current value of the anesthetic depth signal and the target value, and for comparing this difference with predetermined difference threshold values if the anesthetic depth signal is less than the target value, and optionally when the current value of the anesthetic depth signal is below the target value:

reducing with priority the intermediate concentration of the morphinomimetic agent when the difference is less than a third predetermined difference threshold, reducing the intermediate concentration of the morphinomimetic agent and reducing the intermediate concentration of the hypnotic agent in a small proportion when the difference is less than the third predetermined difference threshold and above a fifth predetermined difference threshold, or reducing the intermediate concentration of the morphinomimetic agent and reducing the intermediate concentration of the hypnotic agent in a small proportion when the difference is less than the third predetermined difference threshold and above a fifth predetermined difference threshold, or reducing the intermediate concentration of the morphinomimetic agent and reducing the intermediate concentration of the hypnotic agent in a larger proportion when the difference is less than a fourth predetermined difference threshold, wherein the value of the anesthetic depth signal is brought back into the predetermined range.

11. The system according to claim 1, wherein the system is configured to determine high and low limiting values of concentrations of the hypnotic and morphinomimetic agents.

12. The system according to claim 11, wherein the data input device is configured for the operator to manually input high and low limiting values of concentrations of the hypnotic and morphinomimetic agents.

13. The system according to claim 1 comprising a disabler configured to disable the computer for computing the control signals for controlling the injectors, so as to allow the operator to manually take over control of the injectors.

14. The system according to claim 1, wherein the computer is configured to maintain the control signals at their last value before loss of the signal representative of electrocortical activity of the patient.

15. The system according to claim 14, comprising a sound and/or visual alert component for alerting the operator in a case of the loss of the signal representative of electrocortical activity signal of the patient.

16. The system according to claim 1, wherein the injectors comprise motorized controllers for controlling their operation.

17. A system for controlling injectors of anesthesia and sedation agents in an intravenous anesthesia or sedation mode with a concentration or mass flow rate target, for inducing and maintaining anesthesia or sedation in a patient, the injectors comprising:
   a first injector configured to inject a hypnotic agent, and
   a second injector configured to inject a morphinomimetic agent,
the system comprising:
   a detector configured to acquire a signal representative of electrocortical activity of the patient,
   an analyzer configured to analyze the signal representative of electrocortical activity of the patient in order to extract therefrom an anesthetic depth signal,
   a tracker configured to monitor a value and time-dependent evolution of the anesthetic depth signal,
wherein the tracker is associated with a computer adapted to compute control signals for two specific phases of inducing and maintaining anesthesia: a first phase for induction of anesthesia and a second phase for maintenance of anesthesia, the control signals being computed only based on the anesthetic depth signal obtained from the signal representative of electrocortical activity and a first concentration of the hypnotic agent, the control signal being for:
   controlling the first and second injectors in order to automatically closed-loop regulate injection of the hypnotic agent and the morphinomimetic agent to bring the anesthetic depth signal below a predetermined value during at least one predetermined period of time, during the induction phase of anesthesia or during the maintenance phase of anesthesia, to automatically closed-loop regulate the anesthetic depth signal within a predetermined range around a target value during the maintenance phase of anesthesia, wherein the induction phase of anesthesia is defined as being a period between a beginning of administration of the hypnotic agent and the morphinomimetic agent and maintaining of the anesthetic depth signal, at least 30 seconds below the predetermined value, the predetermined value being equal to 60, and wherein the computer comprises a data input device, wherein an operator can input a type of anesthesia induction selected from a plurality of discrete induction types that correspond to a health state of the patient, wherein the plurality of discrete induction types are distinguished by waiting delay times after reaching a target concentration equilibrium of each agent and by thresholds of index values that determine a change of plateau, said plurality of discrete induction types also differing from each other by an initial concentration of the hypnotic agent, and wherein the computer is configured to determine both (i) an initial concentration of the morphinomimetic agent and (ii) intermediate concentrations of the morphinomimetic agent and the hypnotic agent in order to determine intermediate target values for the anesthetic depth signal in order to define induction plateaus of anesthesia during the induction phase based on the type of anesthesia induction input into the data input device, a time between each induction plateau being between 15 to 120 seconds.

* * * * *